(12) United States Patent
Ignatyev et al.

(10) Patent No.: US 8,143,452 B2
(45) Date of Patent: Mar. 27, 2012

(54) SALTS HAVING ALKOXYTRIS(FLUOROALKYL)BORATE ANIONS

(75) Inventors: Nikola (Mykola) Ignatyev, Duisburg (DE); Urs Welz-Biermann, Heppenheim (DE); Maik Finze, Nienburg (DE); Eduard Bernhardt, Wuppertal (DE); Helge Willner, Muehlheim/Ruhr (DE)

(73) Assignee: Merck Patent GmbH, Darmstadt (DE)

( * ) Notice: Subject to any disclaimer, the term of this patent is extended or adjusted under 35 U.S.C. 154(b) by 204 days.

(21) Appl. No.: 12/715,429

(22) Filed: Mar. 2, 2010

(65) Prior Publication Data

US 2010/0160689 A1   Jun. 24, 2010

Related U.S. Application Data

(62) Division of application No. 11/572,764, filed as application No. PCT/EP2005/007448 on Jul. 9, 2005, now Pat. No. 7,700,781.

(30) Foreign Application Priority Data

Jul. 27, 2004 (DE) .......................... 10 2004 036 299

(51) Int. Cl.
*C07F 5/02* (2006.01)
(52) U.S. Cl. ......................................................... 568/6
(58) Field of Classification Search ................... 568/6
See application file for complete search history.

(56) References Cited

U.S. PATENT DOCUMENTS 7,700,781 B2 * 4/2010 Ignatyev et al. .............. 548/110

OTHER PUBLICATIONS

Adonin, Nicolay Yu, et al., "(Fluoroorgano)fluoroboranes and—borates. 12. Reactions of (Trifluorovinyl)lithium with Chloro-, Chloromethoxy-, and (Trifluorovinyl)methoxyboranes, a Useful Route to (Trifluorovinyl)fluoroborate Salts," Organometallics, Dec. 31, 2003, 535-539, 23(3).
Database CA, Chemical Abstracts Service, Columbus, OH, Ansorge, Andreas, et al., "Complexes of (CF3) 3B with Sterifically Crowded Amines Unexpected Side Products from the Trifluoromethylation of C12BN (ter-Bu) (Bz)," Chemical Sciences 1992, 772-82, 47(6).
Zhou, Z-B, et al., "New Hydrophobic ionic Liquids Based on Perfluoroalkyltrifluoroborate Anions," Journal of Fluorine Chemistry, Elsevier Sequoi, Lausanne, OH, 2004, pp. 471-476, Bd. 125.
Habusha, Uri, et al., "Tuning Carbanion Reactivity by Complexing with Boranes: gamma-elimination Reaction as a Model," Journal of Physical Organic Chemistry, Jul. 21, 2004, pp. 983-989, 17(11).
Ziegler, et al., 1964, CAS: 60:52859.
CAPLUS: Accession No. 2005:221687; Document No. 143:286476 (2005).

* cited by examiner

*Primary Examiner* — Rei-tsang Shiao
(74) *Attorney, Agent, or Firm* — Millen, White, Zelano, Branigan, P.C.

(57) ABSTRACT

The invention relates to salts having alkoxytris(fluoroalkyl) borate anions which on the one hand are used for the synthesis of ionic liquids, but on the other hand can be employed per se as ionic liquid, and to processes for the preparation thereof.

3 Claims, No Drawings

SALTS HAVING ALKOXYTRIS(FLUOROALKYL)BORATE ANIONS

This application is a Divisional of Ser. No. 11/572,764, filed Jan. 26, 2007 now U.S. Pat. No. 7,700,781, which is a National Phase of PCT/EP2005/007448, filed Jul. 9, 2005, which claims benefit of German Application No. 10 2004 036 299.8, filed Jul. 27, 2004, each of which are incorporated herein in their entirety.

The invention relates to salts having alkoxytris(fluoroalkyl)borate anions, and to processes for the preparation thereof.

The salts according to the invention can on the one hand be used for the synthesis of ionic liquids, on the other hand the salts can be employed per se as ionic liquid.

Ionic liquids or liquid salts are ionic species which consist of an organic cation and a generally inorganic anion. They do not contain any neutral molecules and usually have melting points below 373 K.

The area of ionic liquids is currently the subject of intensive research since the potential applications are multifarious. Review articles on ionic liquids are, for example, R. Sheldon "Catalytic reactions in ionic liquids", *Chem. Commun.*, 2001, 2399-2407; M. J. Earle, K. R. Seddon "Ionic liquids. Green solvent for the future", *Pure Appl. Chem.*, 72 (2000), 1391-1398; P. Wasserscheid, W. Keim "Ionische Flüssigkeiten—neue Lösungen für die Übergangsmetallkatalyse" [Ionic Liquids—Novel Solutions for Transition-Metal Catalysis], *Angew. Chem.*, 112 (2000), 3926-3945; T. Welton "Room temperature ionic liquids. Solvents for synthesis and catalysis", *Chem. Rev.*, 92 (1999), 2071-2083 or R. Hagiwara, Ya. Ito "Room temperature ionic liquids of alkylimidazolium cations and fluoroanions", *J. Fluorine Chem.*, 105 (2000), 221-227.

The properties of ionic liquids, for example melting point, thermal and electrochemical stability, viscosity, are strongly influenced by the nature of the anion. By contrast, the polarity and hydrophilicity or lipophilicity can be varied by a suitable choice of the cation/anion pair. As cations, ionic liquids contain, for example, alkylphosphonium, alkylammonium, sulfonium or heterocyclic cations, such as 1,3-dialkylimidazolium or N-alkylpyridinium. Known anions are, for example, $[AlCl_4]^-$, $[Al_2Cl_7]^-$, $NO_3^-$, $BF_4^-$, $PF_6^-$, alkyl- and arylsulfonates, phosphates, imides, methides, carboxylates or also inert carboranes.

E. Bernhardt et al, Z. Anorg. Allg. Chem. 2000, 626, 560, E. Bernhardt et al, Chem. Eur. J. 2001, 7, 4696 and E. Bernhardt et al, Z. Anorg. Allg. Chem. 2003, 629,1229 disclose the novel chemically and electrochemically stable borate anions $[B(CN)_4]^-$, $[F_xB(CN)_{4-x}]^-$, where x=1 to 3, and $[B(CF_3)_4]^-$.

EP 1205480 A1 describes tetrakisfluoroalkylborate salts and the use thereof as conductive salts or ionic liquids.

The object of the present invention was to provide novel and thermally and electrochemically and also hydrolysis-stable salt-like compounds which can be used as ionic liquids or for the synthesis of ionic liquids, and a process for the preparation thereof.

The object is achieved by the salts of the formula (1) according to the invention.

The invention therefore relates to salts of the general formula (1)

$$M^{a+}[RO\text{—}B(R^F)_3]_a \quad (1)$$

in which
$M^{a+}$ denotes a mono- or divalent cation,
a denotes 1 or 2,

R denotes straight-chain or branched alkyl having 1 to 10 C atoms, aryl or aryl-$C_1$-$C_6$-alkyl and
$R^F$ in each case, independently of one another, denotes fluorinated straight-chain or branched alkyl having 1 to 20 C atoms, fluorinated straight-chain or branched $C_1$-$C_6$-alkylaryl or fluorinated aryl-$C_1$-$C_6$-alkyl.

An alkyl group having 1 to 10 C atoms is taken to mean, for example, methyl, ethyl, isopropyl, propyl, butyl, sec-butyl or tert-butyl, furthermore also pentyl, 1-, 2- or 3-methylbutyl, 1,1-, 1,2- or 2,2-dimethylpropyl, 1-ethyl-propyl, hexyl, heptyl, octyl, nonyl or decyl. The alkyl groups may also be partially or fully substituted by halogens, in particular —F and/or —Cl. Fluorinated alkyl groups are difluoromethyl, trifluoromethyl, pentafluoroethyl, pentafluoropropyl, heptafluoropropyl, heptafluorobutyl or nonafluorobutyl.

Aryl denotes phenyl or naphthyl, preferably phenyl.

Aryl-$C_1$-$C_6$-alkyl denotes, for example, benzyl, phenylethyl, phenylpropyl, phenylbutyl, phenylpentyl or phenylhexyl. Fluorinated aryl-$C_1$-$C_6$-alkyl denotes, for example, pentafluorophenyldifluoromethyl or pentafluorophenyltetrafluoroethyl.

Fluorinated straight-chain or branched $C_1$-$C_6$-alkylaryl means that the fluorinated aryl group is substituted by a fluorinated $C_1$-$C_6$-alkyl group, for example —$C_6F_4CF_3$, —$C_6F_4C_2F_5$, —$C_6F_4C_3F_7$, —$C_6F_4C_4F_9$, —$C_6F_4C_5F_{11}$ or —$C_6F_4C_6F_{13}$.

R is preferably straight-chain or branched alkyl having 1 to 10 C atoms, particularly preferably straight-chain or branched alkyl having 1 to 6 C atoms. R is very particularly preferably methyl, ethyl, propyl or i-propyl. R is especially very particularly preferably methyl.

$R^F$ is preferably perfluorinated straight-chain or branched alkyl having 1 to 20 C atoms, particularly preferably perfluorinated straight-chain or branched alkyl having 1 to 6 C atoms. $R^F$ is very particularly preferably trifluoromethyl.

In accordance with the invention, preference is given to a group of compounds of the formula I in which the cation $M^{a+}$ is an alkali metal cation, preferably a lithium, sodium or potassium cation.

This group of compounds is particularly suitable for the synthesis of ionic liquids having the anion according to the invention by metathesis with a salt MX, consisting of an organic cation, as defined below, and the counterion $XF^-$, $Cl^-$, $Br^-$, $I^-$, $[HF_2]^-$, $[CN]^-$, $[SCN]^-$, $[CH_3COO]^-$, $[CH_3SO_3]^-$, $[CF_3COO]^-$, $[CF_3SO_3]^-$, $[CH_3OSO_3]^-$, $[SiF_6]^{2-}$, $[BF_4]^-$, $[SO_4]^{2-}$, $[NO_3]^-$, $[C_2H_5OSO_3]^-$, $[(C_2F_5)_2P(O)O]^-$, $[C_2F_5P(O)O_2]^{2-}$, tosylates, malonates, substituted malonates or $[CO_3]^{2-}$, where electroneutrality should be taken into consideration in the formula of the salt MX. The anion is preferably $F^-$, $Cl^-$, $Br^-$, $I^-$, $[HF_2]^-$, $[CH_3SO_3]^-$, $[CH_3OSO_3]^-$, $[CF_3COO]^-$, $[CF_3SO_3]^-$, $[(C_2F_5)_2P(O)O]^-$ or $[CO_3]^{2-}$, particularly preferably $Cl^-$, $Br^-$, $[CH_3OSO_3]^-$, $[CF_3SO_3]^-$ or $[(C_2F_5)_2P(O)O]^-$.

The lithium compounds in this group are particularly suitable as conductive salts in electrolytes, primary batteries, secondary batteries, capacitors, supercapacitors or electrochemical cells, optionally also in combination with further conductive salts and/or additives, as constituent of a polymer electrolyte or phase-transfer medium.

In accordance with the invention, preference is given to a group of compounds of the formula I in which the cation $M^{a+}$ is a silver, magnesium, copper(I), copper(II), zinc(II) or calcium(II) cation. The copper(II), zinc(II) or calcium(II) cations are preferably in solvated form.

This group of compounds is likewise suitable for the synthesis of ionic liquids having the anion according to the invention by metathesis with a salt MX, as described above for the compounds of the formula I having alkali metal cations.

This group of compounds is particularly suitable for metal deposition or as phase-transfer medium.

In accordance with the invention, preference is given to a group of compounds of the formula I in which the cation $M^{a+}$ is an organic cation.

The organic cation here can be selected from the group $[NR^1R^2R^3R^4]^+$, $[PR^1R^2R^3R^4]^+$, $[P(NR^1R^2)_2(NR^3R^4)_2]^+$, $[C(NR^1R^2)(NR^3R^4)(NR^5R^6)]^+$, $[(R^1R^2N)—C(=OR^7)(NR^3R^4)]^+$ and $[(R^1R^2N)—C(=SR^7)(NR^3R^4)]^+$, where $R^1$ to $R^7$ each, independently of one another, denote hydrogen or straight-chain or branched alkyl having 1 to 20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, where one or more of the substituents $R^1$ to $R^7$ may be partially or fully substituted by halogens, in particular —F and/or —Cl, or partially by —CN or —$NO_2$ and where, in the substituents $R^1$ to $R^6$, one or two non-adjacent carbon atoms which are not in the α-position may be replaced by atoms and/or atom groups selected from the group —O—, —C(O)—, —C(O)O—, —S—, —S(O)—, —$SO_2$—, —$SO_2$O—, —N=, —N=N—, —NH—, —NR'—, —PR'—, —P(O)R'—, —P(O)R'—O—, —O—P(O)R'—O—, —P(O)(NR'$_2$)—NR'— and —PR'$_2$=N—, where R'=non-, partially or perfluorinated $C_1$- to $C_6$-alkyl, $C_3$- to $C_7$-cycloalkyl, unsubstituted or substituted phenyl or an unsubstituted or substituted heterocycle.

A straight-chain or branched alkenyl having 2 to 20 C atoms, where a plurality of double bonds may also be present, is, for example, allyl, 2- or 3-butenyl, isobutenyl, sec-butenyl, furthermore 4-pentenyl, isopentenyl, hexenyl, heptenyl, octenyl, —$C_9H_{17}$, —$C_{10}H_{19}$ to —$C_{20}H_{39}$, preferably allyl, 2- or 3-butenyl, isobutenyl, sec-butenyl, preference is furthermore given to 4-pentenyl, isopentenyl or hexenyl.

A straight-chain or branched alkynyl having 2 to 20 C atoms, where a plurality of triple bonds may also be present, is, for example, ethynyl, 1- or 2-propynyl, 2- or 3-butynyl, furthermore 4-pentynyl, 3-pentynyl, hexynyl, heptynyl, octynyl, —$C_9H_{15}$, —$C_{10}H_{17}$ to —$C_{20}H_{37}$, preferably ethynyl, 1- or 2-propynyl, 2- or 3-butynyl, 4-pentynyl, 3-pentynyl or hexynyl.

Unsubstituted saturated or partially or fully unsaturated cycloalkyl groups having 3-7 C atoms are therefore cyclopropyl, cyclobutyl, cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, phenyl, cycloheptenyl, cyclohepta-1,3-dienyl, cyclohepta-1,4-dienyl or cyclohepta-1,5-dienyl, each of which may be substituted by $C_1$- to $C_6$-alkyl groups, where the cycloalkyl group or the cycloalkyl group which is substituted by $C_1$- to $C_6$-alkyl groups may in turn also be substituted by halogen atoms, such as F, Cl, Br or I, in particular F or Cl, CN or $NO_2$.

The substituents $R^1$ to $R^7$ may be partially or fully substituted by halogen atoms, in particular by F and/or Cl, or partially by CN or $NO_2$.

Furthermore, the substituents $R^1$ to $R^6$ may contain one or two non-adjacent heteroatoms or atom groups selected from the group —O—, —C(O)—, —C(O)O—, —S—, —S(O)—, —$SO_2$—, —$SO_2$O—, —N=, —N=N—, —NH—, —NR'—, —PR'—, —P(O)R'—, —P(O)R'—O—, —O—P(O)R'—O—, —P(O)(NR'$_2$)—NR'— and —PR'$_2$=N—, where R' can be a non-, partially or perfluorinated $C_1$- to $C_6$-alkyl, $C_3$- to $C_7$-cycloalkyl, unsubstituted or substituted phenyl or an unsubstituted or substituted heterocycle, which are not in the α-position to a nitrogen atom or phosphorus atom.

In R', $C_3$- to $C_7$-cycloalkyl is, for example, cyclopropyl, cyclobutyl, cyclopentyl, cyclohexyl or cycloheptyl.

In R', substituted phenyl denotes phenyl which is substituted by $C_1$- to $C_6$-alkyl, $C_1$- to $C_6$-alkenyl, $NO_2$, F, Cl, Br, I, OH, $C_1$-$C_6$-alkoxy, CN, SCN, $SCF_3$, $SO_2CF_3$, C(O)O—$C_1$-$C_6$-alkyl, $NH_2$, $C_1$-$C_6$-alkylamino or $C_1$-$C_6$-dialkylamino, COOH, C(O)NR"$_2$, $SO_2$OR", $SO_2$X', $SO_2$NR"$_2$, $SO_3$H or NHC(O)R", where X' denotes F, Cl or Br and R" denotes a non-, partially or perfluorinated $C_1$- to $C_6$-alkyl or $C_3$- to $C_7$-cycloalkyl, as defined for R', for example o-, m- or p-methylphenyl, o-, m- or p-ethylphenyl, o-, m- or p-propylphenyl, o-, m- or p-isopropylphenyl, o-, m- or p-tert-butylphenyl, o-, m- or p-aminophenyl, o-, m- or p-(N,N-dimethylamino)phenyl, o-, m- or p-nitrophenyl, o-, m- or p-hydroxyphenyl, o-, m- or p-methoxyphenyl, o-, m- or p-ethoxyphenyl, o-, m-, p-(trifluoromethyl)phenyl, o-, m-, p-(trifluoromethoxy)phenyl, o-, m-, p-(trifluoromethylsulfonyl)phenyl, o-, m- or p-fluorophenyl, o-, m- or p-chlorophenyl, o-, m- or p-bromophenyl, o-, m- or p-iodophenyl, furthermore preferably 2,3-, 2,4-, 2,5-, 2,6-, 3,4- or 3,5-dimethylphenyl, 2,3-, 2,4-, 2,5-, 2,6-, 3,4- or 3,5-dihydroxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethylphenyl.

In R', heterocycle is taken to mean a saturated or unsaturated mono- or bi-cyclic heterocyclic radical having 5 to 13 ring members, in which 1, 2 or 3 N and/or 1 or 2 S or O atoms may be present and the heterocyclic radical may be mono- or polysubstituted by $C_1$- to $C_6$-alkyl, $C_1$- to $C_6$-alkenyl, $NO_2$, F, Cl, Br, I, OH, $C_1$-$C_6$-alkoxy, CN, SCN, $SCF_3$, $SO_2CF_3$, C(O)O—$C_1$-$C_6$-alkyl, $NH_2$, $C_1$-$C_6$-alkylamino or $C_1$-$C_6$-dialkylamino, COOH, C(O)NR"$_2$, $SO_2$OR", $SO_2$X', $SO_2$NR"$_2$, $SO_3$H or NHC(O)R", where X' and R" have an above-mentioned meaning.

The heterocyclic radical is preferably substituted or unsubstituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl or 1-, 2- or 3-pyrrolidinyl.

Without restricting generality, examples of substituents $R^1$ to $R^6$ or also below of substituents $R^{1'}$ to $R^{4'}$ are:

—CH$_3$, —C$_2$H$_5$, —C$_3$H$_7$, —CH(CH$_3$)$_2$, —C$_4$H$_9$, —C(CH$_3$)$_3$, —C$_5$H$_{11}$, —C$_6$H$_{13}$, —C$_7$H$_{15}$, —C$_8$H$_{17}$, —C$_9$H$_{19}$, —C$_{10}$H$_{21}$, —C$_{12}$H$_{25}$, —C$_{20}$H$_{41}$, —CH$_2$OCH$_3$, —C$_2$H$_4$OCH(CH$_3$)$_2$, —C$_2$H$_4$SC$_2$H$_5$, —C$_2$H$_4$SCH(CH$_3$)$_2$, —CH$_2$SO$_2$CH$_3$, —CH$_2$N(H)C$_2$H$_5$, —C$_2$H$_4$N(H)C$_2$H$_5$, —CH$_2$N(CH$_3$)CH$_3$, —CN, —C$_2$H$_4$N(CH$_3$)CH$_3$, —CF$_3$, —C$_2$F$_5$, —C$_3$F$_7$, —C$_4$F$_9$, —C(CF$_3$)$_3$, —CF$_2$SO$_2$CF$_3$, —C$_2$F$_4$N(C$_2$F$_5$)C$_2$F$_5$, —CHF$_2$, —CH$_2$CF$_3$, —C$_2$F$_2$H$_3$, —C$_3$FH$_6$, —CH$_2$C$_3$F$_7$, —C(CFH$_2$)$_3$, —CH$_2$C(O)OH, —CH$_2$C$_6$H$_5$, —CH$_2$C(O)CH$_3$, —CH$_2$C(O)C$_2$H$_5$, —CH$_2$C(O)OCH$_3$, CH$_2$C(O)OC$_2$H$_5$, —C(O)CH$_3$, —C(O)C$_6$H$_5$, —C(O)OCH$_3$, —C(O)OC$_2$H$_5$,

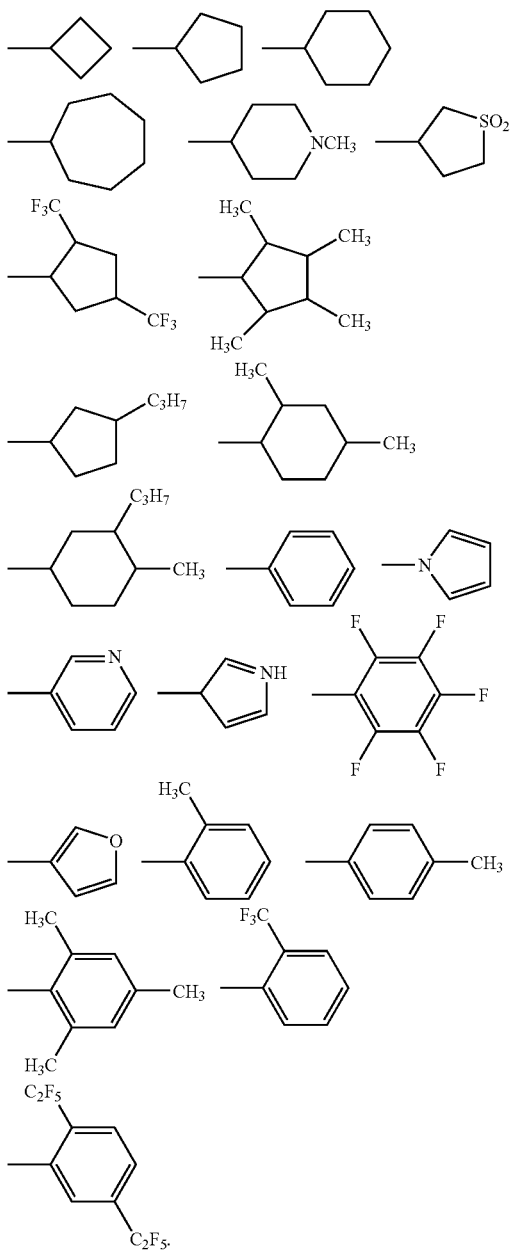

Up to four substituents of the guanidinium cation [C(NR$^1$R$^2$)(NR$^3$R$^4$)—(NR$^5$R$^6$)]$^+$ may also be connected in pairs in such a way that mono-, bi- or polycyclic cations are formed.

Without restricting generality, examples of such guanidinium cations are:

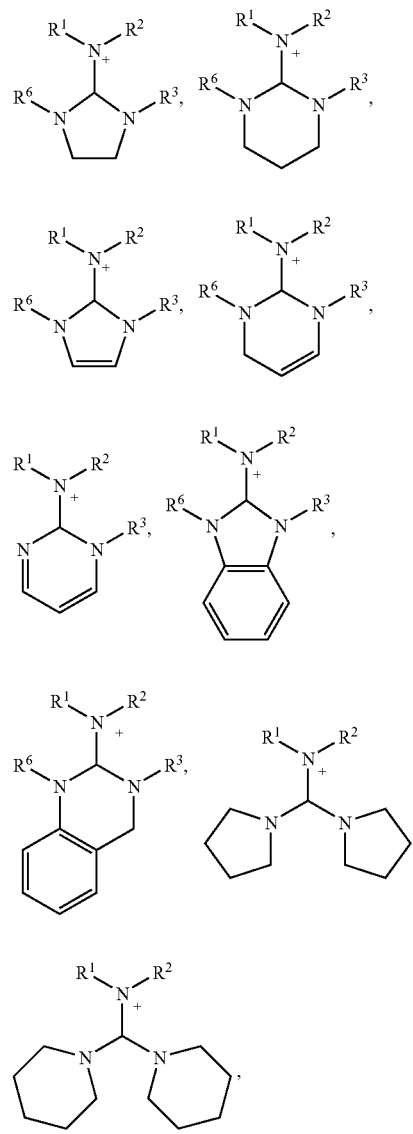

where the substituents R$^1$ to R$^3$ and R$^6$ may have an above-mentioned or particularly preferred meaning.

The carbocycles or heterocycles of the above-mentioned guanidinium cations may optionally also be substituted by C$_1$- to C$_6$-alkyl, C$_1$- to C$_6$-alkenyl, NO$_2$, F, Cl, Br, I, OH, C$_1$-C$_6$-alkoxy, CN, SCN, SCF$_3$, SO$_2$CF$_3$, C(O)O—C$_1$-C$_6$-alkyl, NH$_2$, C$_1$-C$_6$-alkylamino or C$_1$-C$_6$-dialkylamino, COOH, C(O)NR''$_2$, SO$_2$OR'', SO$_2$NR''$_2$, SO$_2$X', SO$_3$H or NHC(O)R'', where X' and R'' have an above-mentioned meaning, substituted or unsubstituted phenyl or an unsubstituted or substituted heterocycle.

Up to four substituents of the uronium cation [(R$^1$R$^2$N)—C(=OR$^7$)(NR$^3$R$^4$)]$^+$ or of the thiouronium cation [(R$^1$R$^2$N)—C(=SR$^7$)(NR$^3$R$^4$)]$^+$ may also be connected in pairs in such a way that mono-, bi- or polycyclic cations are formed. Without restricting generality, examples of such cations are indicated below, where X=O or S:

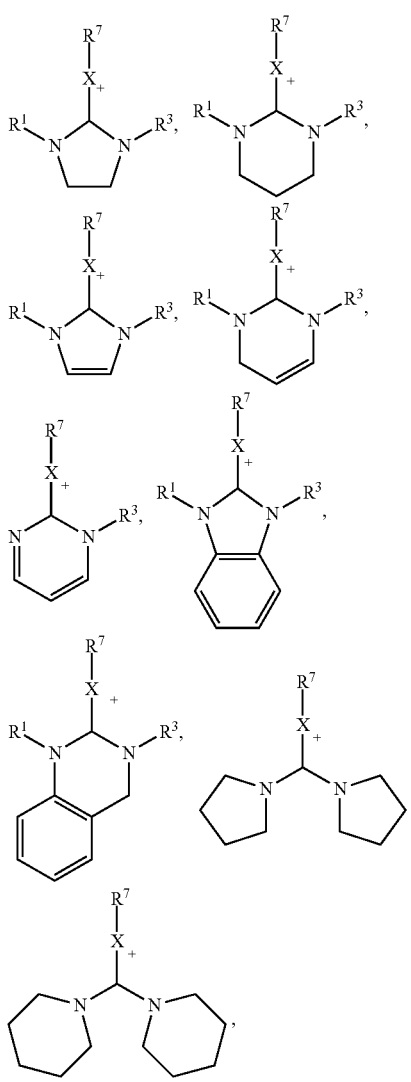

where the substituents $R^1$, $R^3$ and $R^7$ may have an abovementioned or particularly preferred meaning.

The carbocycles or heterocycles of the above-mentioned cations may optionally also be substituted by $C_1$- to $C_6$-alkyl, $C_1$- to $C_6$-alkenyl, $NO_2$, F, Cl, Br, I, OH, $C_1$-$C_6$-alkoxy, CN, SCN, $SCF_3$, $SO_2CF_3$, C(O)O—$C_1$-$C_6$-alkyl, $NH_2$, $C_1$-$C_6$-alkylamino or $C_1$-$C_6$-dialkylamino, COOH, C(O)NR″$_2$, $SO_2OR″$, $SO_2NR″_2$, $SO_2X'$, $SO_3H$ or NHC(O)R″ or substituted or unsubstituted phenyl or an unsubstituted or substituted heterocycle, where X' and R″ have an above-mentioned meaning.

The organic cation is particularly preferably selected from the group of the ammonium, phosphonium and guanidinium salts.

The substituents $R^1$ to $R^7$ are each, independently of one another, preferably a straight-chain or branched alkyl group having 1 to 10 C atoms. $R^1$ to $R^7$ are particularly preferably methyl, ethyl, propyl, i-propyl or butyl.

The substituents $R^1$ to $R^4$ in the formulae $[NR^1R^2R^3R^4]^+$ or $[PR^1R^2R^3R^4]^+$ are particularly preferably identical.

As a consequence of the synthesis, preference is given to a group of salts in which one substituent $R^1$, $R^2$, $R^3$, $R^4$, $R^5$ or $R^6$ or, in the case of uronium and thiouronium, $R^7$ is identical to the substituent R of the anion.

The organic cation can furthermore be selected from the group of the heterocyclic cations. Heterocyclic cations are, for example,

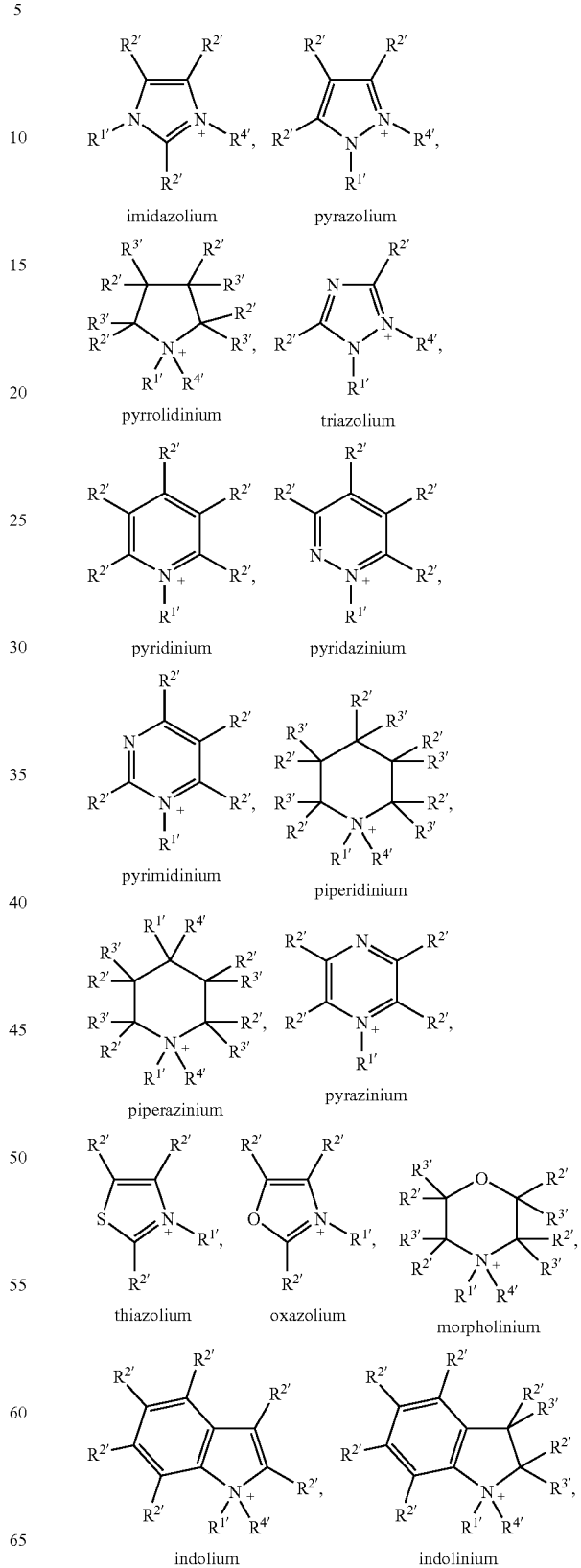

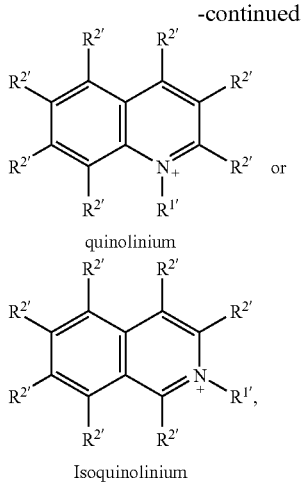

quinolinium

Isoquinolinium where the substituents $R^{1'}$ to $R^{4'}$ each, independently of one another, denote hydrogen, straight-chain or branched alkyl having 1-20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, saturated, partially or fully unsaturated heteroaryl, heteroaryl-$C_1$-$C_6$-alkyl or aryl-$C_1$-$C_6$-alkyl, where one or more substituents $R^{1'}$ to $R^{4'}$ may be partially or fully substituted by halogens, in particular —F and/or —Cl, or partially by —CN or —NO$_2$, and where, in the substituents $R^{1'}$ to $R^{4'}$, one or two non-adjacent carbon atoms which are not bonded to the heteroatom in the α-position may be replaced by atoms and/or atom groups selected from the group —O—, —C(O)—, —C(O)O—, —S—, —S(O)—, —SO$_2$—, —SO$_2$O—, —N=, —N=N—, —NH—, —NR'—, —PR'—, —P(O)R'—, —P(O)R'—O—, —O—P(O)R'—O—, —P(O)(NR'$_2$)—NR'— and —PR'$_2$=N—, where R'=non-, partially or perfluorinated $C_1$- to $C_6$-alkyl, $C_3$- to $C_7$-cycloalkyl, unsubstituted or substituted phenyl or an unsubstituted or substituted heterocycle.

The substituents $R^{1'}$ to $R^{4'}$ are particularly preferably a straight-chain or branched alkyl group having 1 to 20 C atoms, very particularly preferably having 1 to 12 C atoms.

As a consequence of the synthesis, preference is given to a group of compounds in which one substituent $R^{1'}$ or $R^{4'}$ is identical to the substituent R of the anion component. Preference is furthermore given to salts of the formula (1) having heterocyclic cations, as defined above, in which the substituents $R^{1'}$ and $R^{4'}$ are different.

From the group of heterocyclic organic cations, the cations are particularly preferably selected from substituted imidazolium, substituted pyridinium, substituted pyrrolidinium, substituted piperidinium and substituted morpholinium, as defined above.

The salts of the formula (1) according to the invention having organic cations, as described above, can be used as ionic liquids. Ionic liquids can be employed, for example, as solvents for many synthetic or catalytic reactions, for example Friedel-Crafts acylation and alkylation, Diels-Alder cycloadditions, hydrogenation and oxidation reactions, Michael-type reactions or Heck reactions, as non-aqueous electrolytes, which are optionally employed in combination with other conductive salts known to the person skilled in the art, additives and solvents.

In addition, the ionic liquids according to the invention can be used as nonaqueous polar substances in suitable reactions, as phase-transfer catalyst, as surfactant (surface-active agent) or as medium for the heterogenisation of homogeneous catalysts.

They are furthermore suitable as desiccants and as separation media for gases.

The present invention secondly relates to a process for the preparation of the salts of the formula (1) according to the invention, characterised in that a dialkyloxonium tris(fluoroalkyl)borate of the formula (2)

$$(R)_2O\text{—}B(R^F)_3 \qquad (2)$$

where R and $R^F$ have a meaning indicated for the compounds of the formula (1), is reacted with an inorganic salt containing the metal cation $M^{a+}$, as described above, or with an alkylatable organic compound, for example an amine, phosphine, guanidine, urea, thiourea or a heterocycle, corresponding to the cations, as described above.

Suitable inorganic salts for the preparation of the compounds of the formula (1) in which $M^{a+}$ is an alkali metal cation or a cation from the group silver, magnesium, copper, zinc and calcium are, for example, $Na_2CO_3$, $K_2CO_3$, KOH, NaOH, $Ag_2O$, $Ag_2CO_3$, $MgCO_3$, KCl, CuO, $ZnCO_3$ or $Ca(CO_2CH_3)_2$.

The reaction is preferably carried out in an organic solvent, for example dichloromethane, a dialkyl ether, for example diethyl ether, ethyl acetate, water or an alcohol, for example methanol or ethanol, at a temperature between 0° C. and 100° C., preferably between 10° and 80° C., particularly preferably at room temperature.

Suitable alkylatable organic starting materials for the synthesis of compounds of the formula (1) having organic cations are [$NR^1R^2R^3$], [$PR^1R^2R^3$], [$P(NR^1R^2)_2(NR^3R^4)$], [$C(NR^1R^2)(=NR^4)(NR^5R^6)$], [$(R^1R^2N)\text{—}C(=O)(NR^3R^4)$] or [$(R^1R^2N)\text{—}C(=S)(NR^3R^4)$] and, for example, the heterocyclic compounds

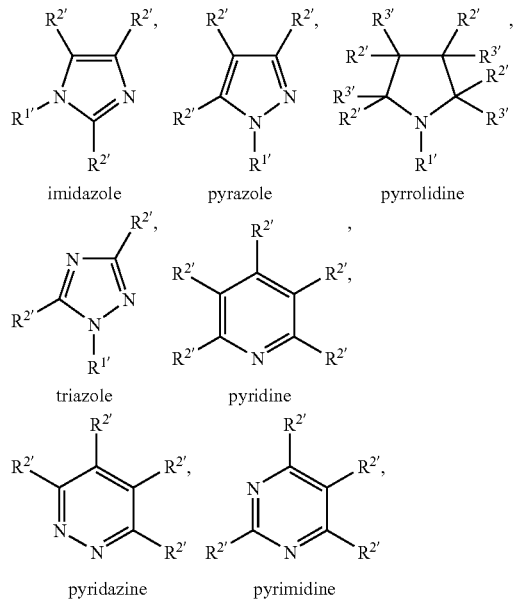

imidazole    pyrazole    pyrrolidine triazole    pyridine pyridazine    pyrimidine

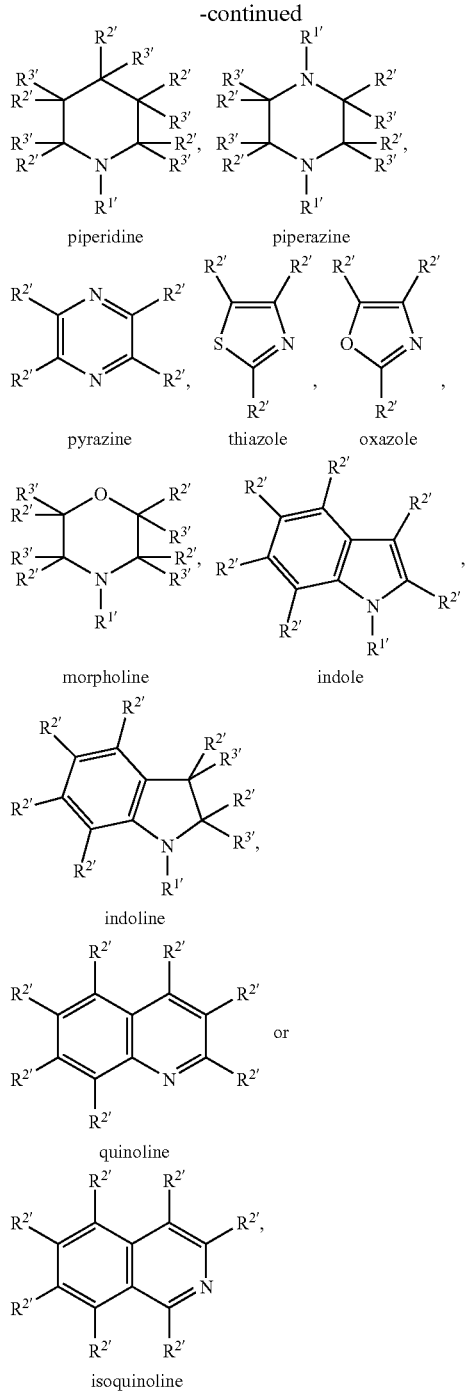

where the substituents $R^1$ to $R^6$ and $R^{1'}$ to $R^{4'}$ are as defined above for the cations.

The reaction is preferably carried out under inert-gas conditions in an organic solvent, for example dichloromethane, a dialkyl ether, for example diethyl ether, ethyl acetate, nitromethane or acetonitrile, at a temperature between 0° C. and 100° C., preferably between 10° and 80° C., particularly preferably at room temperature.

This alkylation process inevitably gives compounds of the formula (1) having an organic cation, where one substituent, depending on the starting material, for example $R^4$ of the phosphonium or ammonium cations, $R^7$ of the uronium or thiouronium cations, or $R^{1'}$ or $R^{4'}$ of the heterocyclic cations, is identical to the substituent R of the anion component.

The dialkyloxonium tris(fluoroalkyl)borates of the formula (2)

$$(R)_2O-B(R^F)_3 \qquad (2),$$

where R and $R^F$ have a preferred or particularly preferred meaning, as indicated for the compounds of the formula (1), are novel. Dialkyloxonium tris(fluoroalkyl)borates are stable at room temperature and are excellent alkylating agents. One application of these compounds is in the synthesis of the compounds of the formula (1). However, they can also be employed as general alkylating agents in other organic syntheses.

The invention therefore also relates to compounds of the formula (2)

$$(R)_2O-B(R^F)_3 \qquad (2),$$

in which

R denotes straight-chain or branched alkyl having 1 to 10 C atoms, aryl or aryl-$C_1$-$C_6$-alkyl and $R^F$ in each case, independently of one another, denotes fluorinated straight-chain or branched alkyl having 1 to 20 C atoms, fluorinated straight-chain or branched $C_1$-$C_6$-alkylaryl or fluorinated aryl-$C_1$-$C_6$-alkyl.

In compounds of the formula (2), R is preferably a straight-chain or branched alkyl having 1 to 6 C atoms; $R^F$ is preferably perfluorinated alkyl having 1 to 6 C atoms. The substituents $R^F$ are preferably identical.

Dialkyloxonium tris(fluoroalkyl)borates of the formula (2) are obtained by reaction of a tris(fluoroalkyl)boron carbonyl of the formula (3)

$$(R^F)_3BCO \qquad (3),$$

where $R^F$ in each case, independently of one another, has a meaning indicated for formula (1), with a dialkyl ether of the formula (4)

$$(R)_2O \qquad (4),$$

where R in each case, independently of one another, has a meaning indicated for formula (1).

Carbonyltris(trifluoromethyl)borane and a process for the preparation thereof is known from J. Am. Chem. Soc, 2002, 51, 15385 or Angew. Chem. 2002, 114, 823. The other tris(fluoroalkyl)boron carbonyls of the formula (3) can be prepared analogously to carbonyltris(trifluoromethyl)borane.

The dialkyl ether is preferably condensed into the boron carbonyl at temperatures between –200° and 25° C. or added to the boron carbonyl at room temperature in a suitable solvent. The reaction mixture is then warmed to temperatures between 10° and 40°, particularly preferably to room temperature, and stirred at this temperature for 10 to 14 hours.

The desired product can be purified using conventional methods, as known to the person skilled in the art. The purification is preferably carried out by recrystallisation.

In accordance with the invention, the reagents in the alkylation can be reacted in a mixing ratio of up to a five-fold excess of one of the reactants, in particular the alkylating agent. However, the reactants are preferably employed in equimolar amount.

By-products which form are, for example, the products $[(R)_3O]^+[(R^F)_3BOR]^-$, $[(R)_3O]^+[(R^F)_3BC(O)OR]^-$ and/or $(R^F)_3BC(OR)_2$, where the substituents R and $R^F$ have a meaning indicated for formula (1).

These by-products are likewise strong alkylating agents.

The invention furthermore relates to a process for the preparation of compounds of the formula (1) in which $M^{a+}$ is an organic cation without the restriction that a substituent of the organic cation is identical to the substituent R of the anion component, characterised in that a compound of the formula (1)

$$M^{a+}[RO-B(R^F)_3]_a \quad (1),$$

in which $M^{a+}$ denotes an alkali metal cation, a silver, magnesium, copper, zinc or calcium cation, optionally in solvated form, R denotes straight-chain or branched alkyl having 1 to 10 C atoms, aryl or aryl-$C_1$-$C_6$-alkyl and $R^F$ in each case, independently of one another, denotes fluorinated straight-chain or branched alkyl having 1 to 20 C atoms, fluorinated straight-chain or branched $C_1$-$C_6$-alkylaryl or fluorinated aryl-$C_1$-$C_6$-alkyl, is reacted with a compound of the formula (5)

$$MX \quad (5),$$

in which

M is an organic cation, as defined above, and the anion X denotes $F^-$, $Cl^-$, $Br^-$, $I^-$, $[HF_2]^-$, $[CN]^-$, $[SCN]^-$, $[CH_3COO]^-$, $[CH_3SO_3]^-$, $[CF_3COO]^-$, $[CF_3SO_3]^-$, $[CH_3OSO_3]^-$, $[SiF_6]^{2-}$, $[BF_4]^-$, $[SO_4]^{2-}$, $[NO_3]^-$, $[C_2H_5OSO_3]^-$, $[(C_2F_5)_2P(O)O]^-$, $[C_2F_5P(O)O_2]^{2-}$, tosylates, malonates, substituted malonates or $[CO_3]^{2-}$, where electroneutrality should be taken into consideration in the formula of the salt MX.

The anion in the formula (5) is preferably $F^-$, $Cl^-$, $Br^-$, $I^-$, $[HF_2]^-$, $[CH_3SO_3]^-$, $[CH_3OSO_3]^-$, $[CF_3COO]^-$, $[CF_3SO_3]^-$, $[(C_2F_5)_2P(O)O]^-$ or $[CO_3]^{2-}$, particularly preferably $Cl^-$, $Br^-$, $[CH_3OSO_3]^-$, $[CF_3SO_3]^-$ or $[(C_2F_5)_2P(O)O]^-$.

The reaction is advantageously carried out in water, where temperatures of 10°-100° C., preferably 15°-60° C., particularly preferably room temperature, are suitable.

However, the reaction can alternatively also be carried out in organic solvents at temperatures between 10° and 100° C. Suitable solvents here are benzene, acetonitrile, dioxane, dichloromethane, dimethoxyethane or an alcohol, for example methanol or ethanol.

The complete disclosure content of all applications, patents and publications mentioned above and below is incorporated into this application by way of reference.

Even without further comments, it is assumed that a person skilled in the art will be able to utilise the above description in the broadest scope. The preferred embodiments and examples should therefore merely be regarded as descriptive disclosure which is absolutely not limiting in any way.

The NMR spectra were measured on solutions in deuterated solvents at 20° C. in a Bruker Avance 300 spectrometer with a 5 mm $^1$H/BB broad-band head with deuterium lock, unless indicated otherwise in the examples. The measurement frequencies of the various nuclei are: $^1$H: 300.13 MHz, $^{11}$B: 96.92 MHz, $^{19}$F: 282.41 MHz and $^{31}$P: 121.49 MHz. The referencing method is indicated separately for each spectrum or for each data set.

EXAMPLE 1

Synthesis of dimethyloxonium tris(trifluoromethyl)borate, $(CH_3)_2OB(CF_3)_3$

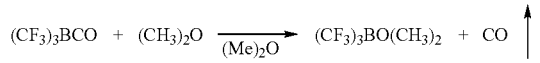

5 ml of dimethyl ether are condensed into 2.75 g (11.2 mmol) of tris(trifluoromethyl)boron carbonyl, $(CF_3)_3BCO$, at −196° C. The reaction mixture warms to room temperature, and stirring is continued overnight. The volatile constituents are distilled off in vacuo, giving 2.74 g of a solid which consists of 95.9% of $(CF_3)_3BO(CH_3)_2$. The crude product can be freed from by-products by recrystallisation from a dichloromethane/pentane mixture. The yield, based on tris(trifluoromethyl)boron carbonyl, is 89%.

Elemental analysis:
found: C, 22.41; H, 2.24.
calculated ($C_5H_6BF_9O$): C, 22.76; H, 2.29.
$^1$H-NMR ($CD_2Cl_2$, reference: TMS), δ [ppm]: 3.87 br.s.
$^{11}$B-NMR ($CD_2Cl_2$, reference: $BF_3$.OEt$_2$ external), δ [ppm]: −5.1.
$^{19}$F-NMR ($CD_2Cl_2$, reference: $CFCl_3$), δ [ppm]: −64.2 s.
$^{13}$C-NMR of $(CF_3)_3BO(CD_3)_2$ ($CD_2Cl_2$, reference: TMS), δ [ppm]: 72.0 ($CD_3$), 128.1 ($CF_3$).

EXAMPLE 2

Synthesis of 1-butyl-3-methylimidazolium methoxytris(trifluoromethyl)borate

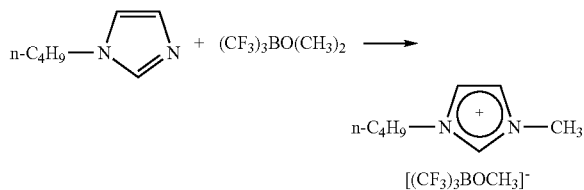

0.211 g (1.70 mmol) of 1-n-butylimidazole is added with stirring under an inert-gas atmosphere to a solution of 0.448 g (1.70 mmol) of dimethyloxonium tris(trifluoromethyl)borate in 3 ml of dry dichloromethane. The reaction mixture is stirred overnight at room temperature, and the volatile products are subsequently distilled off in vacuo, giving 0.66 g of liquid 1-butyl-3-methylimidazolium methoxytris(trifluoromethyl)borate (m.p.<20° C.). The yield is approximately quantitative.

Elemental analysis:
found: C, 36.89; H, 4.95; N, 7.49.
calculated ($C_{12}H_{18}BF_9N_2O$): C, 37.14; H, 4.68; N, 7.22.
$^1$H-NMR ($CD_3CN$, reference: TMS), δ [ppm]: 0.94 t (3H, $CH_3$), 1.26-1.40 m (2H, $CH_2$), 1.76-1.86 m (2H, $CH_2$), 3.33 br. s (3H, $OCH_3$), 3.82 s (3H, $NCH_3$), 4.12 t (2H, $NCH_2$), 7.29-7.41 m (2H), 8.43 s (1H).
$^{11}$B-NMR ($CD_3CN$, reference: $BF_3$.OEt$_2$ external), δ [ppm]: −9.5.
$^{19}$F-NMR ($CD_3CN$, reference: $CFCl_3$), δ [ppm]: −65.1 s.

EXAMPLE 3

Synthesis of tri-n-butylmethylphosphonium methoxytris(trifluoromethyl)borate

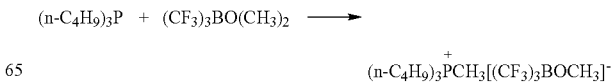

0.276 g (1.36 mmol) of tri-n-butylphosphine in 3 ml of dry dichloromethane is added with stirring under an inert-gas atmosphere to a solution of 0.360 g (1.36 mmol) of dimethyloxonium tris(trifluoromethyl)borate in 3 ml of dry dichloromethane. The reaction mixture is stirred overnight at room temperature, and the volatile products are subsequently distilled off in vacuo, giving 0.643 g of tri-n-butylmethylphosphonium methoxytris(trifluoromethyl)borate (m.p. 63° C.). The yield is approximately quantitative.

Elemental analysis:

found: C, 44.03; H 7.08.

calculated ($C_{17}H_{33}BF_9OP$): C, 43.80; H, 7.13.

$^1$H-NMR ($CD_3CN$, reference: TMS), δ [ppm]: 0.95 t (9H, $CH_3$), 1.35-1.60 m (12H, $6CH_2$), 1.68 d (3H, $PCH_3$), 1.98-2.13 m (6H, $3CH_2$), 3.33 br. s (3H, $OCH_3$), $^2J_{P,H}$=13.5 Hz.

$^{11}$B-NMR ($CD_3CN$, reference. $BF_3.OEt_2$ external), δ [ppm]: −9.5.

$^{19}$F-NMR ($CD_3CN$, reference: $CFCl_3$), δ [ppm]: −65.1 s.

EXAMPLE 4

Synthesis of potassium methoxytris(trifluoromethyl)borate

5 ml of a concentrated aqueous potassium carbonate solution are added with stirring at room temperature to a solution of 1.09 g (4.13 mmol) of dimethyloxonium tris(trifluoromethyl)borate in 10 ml of dichloromethane. The reaction mixture is stirred for one hour and extracted three times with 150 ml, 100 ml and 50 ml of diethyl ether. The extract is dried over $K_2CO_3$. After the solid has been filtered off, the solvent is distilled off in vacuo, giving 1.11 g of potassium methoxytris(trifluoromethyl)borate, which corresponds to a yield of 93.3%.

Elemental analysis:

found: C, 16.99; H, 1.05.

calculated ($C_4H_3BF_9OK$): C, 16.68; H, 1.05.

$^1$H-NMR ($CD_3CN$, reference: TMS), δ [ppm]: 3.33 br.s.

$^{11}$B-NMR ($CD_3CN$, reference. $BF_3.OEt_2$ external), δ [ppm]: −9.5.

$^{19}$F-NMR ($CD_3CN$, reference: $CFCl_3$), δ [ppm]: −65.1 s.

$^{13}$C-NMR of $K[(CF_3)_3BOCD_3]$ ($CD_3CN$, reference: TMS), δ [ppm]: 51.3 ($CD_3$), 133.6 ($CF_3$).

EXAMPLE 5

Synthesis of tetra-n-butylammonium methoxytris(trifluoromethyl)borate

0.215 g (0.78 mmol) of tetra-n-butylammonium chloride in 5 ml of water is added to a solution of 0.245 g (0.85 mmol) of potassium methoxytris(trifluoromethyl)borate in 5 ml of water. After two hours, the precipitate is filtered off and washed with 50 ml of water and dried in vacuo, giving 0.359 g of tetra-n-butylammonium methoxytris(trifluoromethyl)borate (m.p. 134° C.), which corresponds to a yield of 94.2%.

Elemental analysis:

found: C, 48.92; H, 7.96; N 2.85.

calculated ($C_{20}H_{39}BF_9NO$): C, 48.89; H, 8.00; N, 2.85.

$^1$H-NMR ($CD_3CN$, reference: TMS), δ [ppm]: 0.97 t (12H, $4CH_3$), 1.28-1.42 m (8H, $4CH_2$), 1.53-1.66 m (8H, $4CH_2$), 3.02-3.12 m (8H, $4CH_2$), 3.33 br. s (3H, $OCH_3$).

$^{11}$B-NMR ($CD_3CN$, reference: $BF_3.OEt_2$ external), δ [ppm]: −9.5.

$^{19}$F-NMR ($CD_3CN$, reference: $CFCl_3$), δ [ppm]: −65.1 s.

The invention claimed is:

1. A compound of the formula (2)

in which

R denotes straight-chain or branched alkyl having 1 to 10 C atoms, aryl or aryl-$C_1$-$C_6$-alkyl and $R^F$ in each case, independently of one another, denotes fluorinated straight-chain or branched alkyl having 1 to 20 C atoms, fluorinated straight-chain or branched $C_1$-$C_6$-alkyl(aryl) or fluorinated aryl-$C_1$-$C_6$-alkyl.

2. A process for the preparation of compounds of the formula (2), wherein a tris(fluoroalkyl)boron carbonyl of the formula (3)

where $R^F$ in each case, independently of one another, denotes fluorinated straight-chain or branched alkyl having 1 to 20 C atoms, fluorinated straight-chain or branched $C_1$-$C_6$-alkyl(aryl) or fluorinated aryl-$C_1$-$C_6$-alkyl, is reacted with a dialkyl ether of the formula (4)

where R in each case, independently of one another, denotes straight-chain or branched alkyl having 1 to 10 C atoms, aryl or aryl-$C_1$-$C_6$-alkyl.

3. An alkylating agent comprising a compound according to claim 1.

* * * * *